United States Patent [19]

Burd

[11] Patent Number: 4,985,129
[45] Date of Patent: Jan. 15, 1991

[54] APPARATUS FOR CAPILLARY ELECTROPHORESIS

[75] Inventor: Samuel Burd, Oakland, Calif.
[73] Assignee: Bio-Rad Laboratories, Inc., Hercules, Calif.
[21] Appl. No.: 279,382
[22] Filed: Dec. 2, 1988
[51] Int. Cl.[5] .................... G01N 27/28; G01N 27/26; B01D 57/02
[52] U.S. Cl. .............................. 204/299 R; 204/180.1; 204/183.3
[58] Field of Search .............. 204/299 R, 180.1, 183.3

[56] References Cited

U.S. PATENT DOCUMENTS 3,998,714 12/1976 Deml et al. .................... 204/299 R
4,676,897 6/1987 Kuze et al. .................... 204/183.3 X

FOREIGN PATENT DOCUMENTS 1562418 4/1969 France.

OTHER PUBLICATIONS

Verhaggen, P.E.M., "Simple Sampling Device for Capillary Isotachophoresis and Capillary Zone Electrophoresis", Journal of Chromatography, 452(1988), 614–622.

Primary Examiner—John F. Niebling
Assistant Examiner—John S. Starsiak, Jr.
Attorney, Agent, or Firm—Townsend and Townsend

[57] ABSTRACT

A capillary tube for use in high performance capillary electrophoresis is enclosed in a cartridge of generally planar configuration, formed by two flat plates joined together along raised edges to define a shallow enclosed chamber to retain the looped capillary tube, the plates having aligned windows between which a segment of the capillary tube passes, thereby forming a light path for zone detection. The termini of the capillary are embedded in fittings extending from the exterior of the cartridge, which mate with complementary fittings on inlet and outlet blocks which contain buffer reservoirs with controlled hydrostatic heads. The inlet block is specially equipped with ducts and fittings to permit filling of the capillary, injection of the sample into the capillary, changing of the solution in the buffer reservoir, and flushing out of the entire block without disconnecting the block from the capillary cartridge. By securing the cartridge containing the capillary tube into its holder, the capillary tube is correctly aligned in the detector light path.

9 Claims, 4 Drawing Sheets

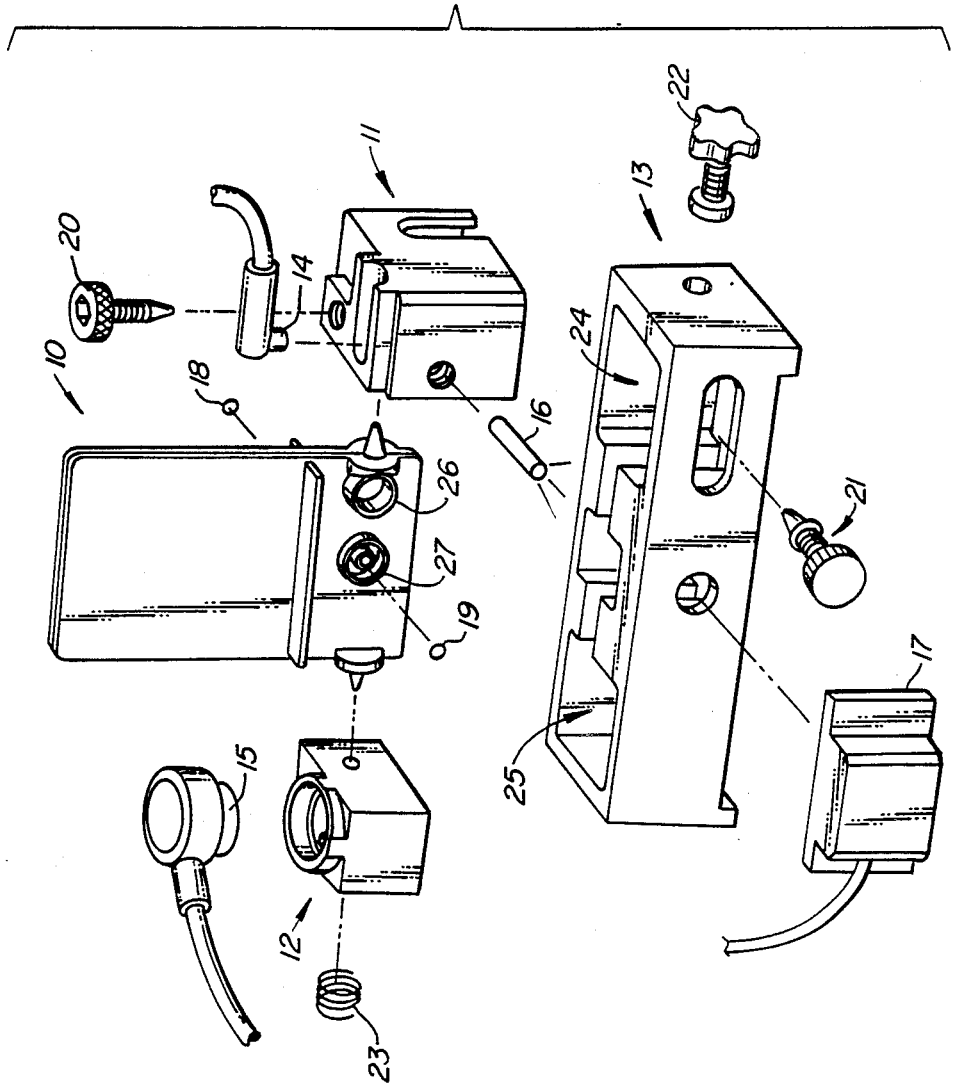
FIG.—1

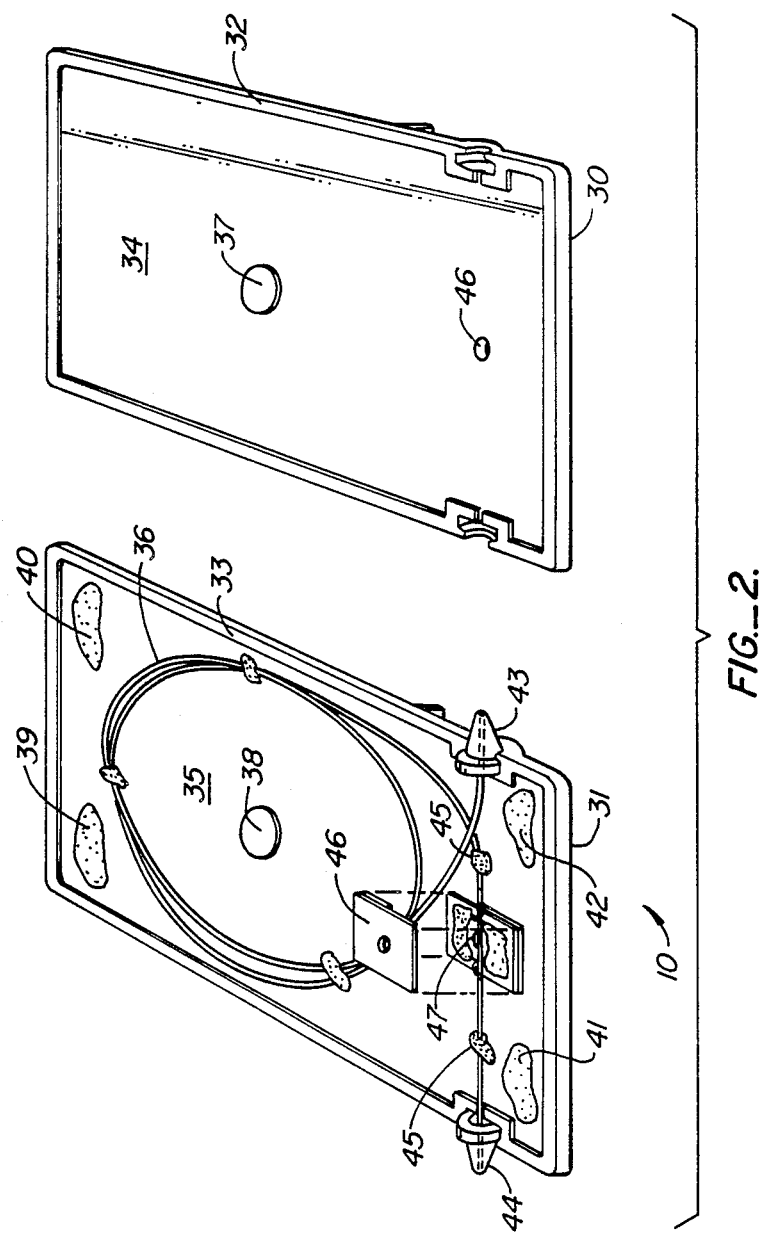
FIG._2.

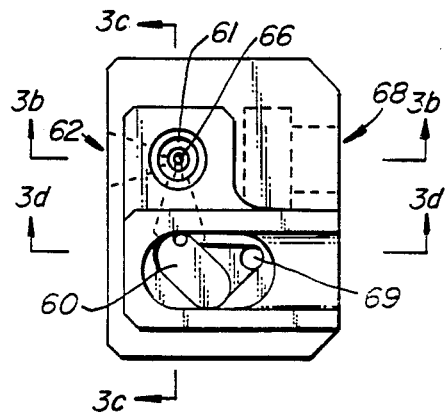
FIG._3a.
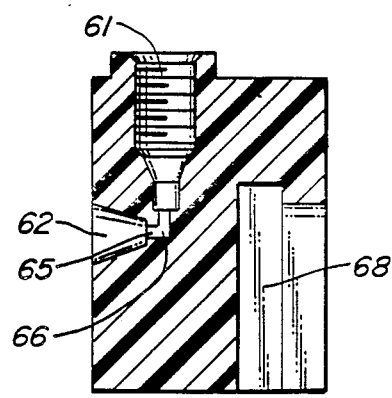
FIG._3b.
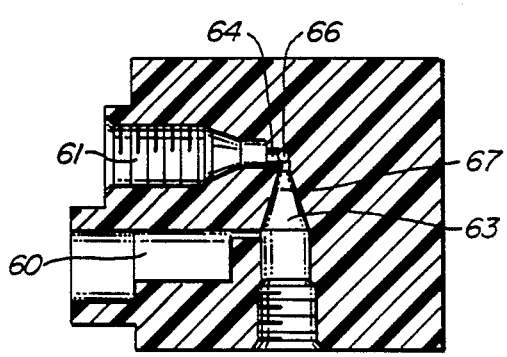
FIG._3c.
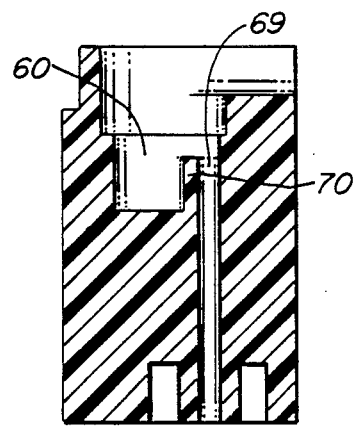
FIG._3d.

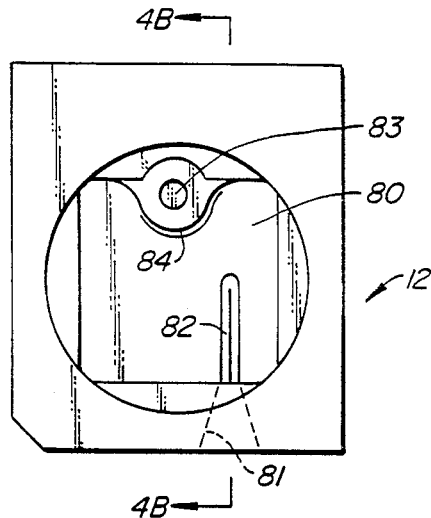
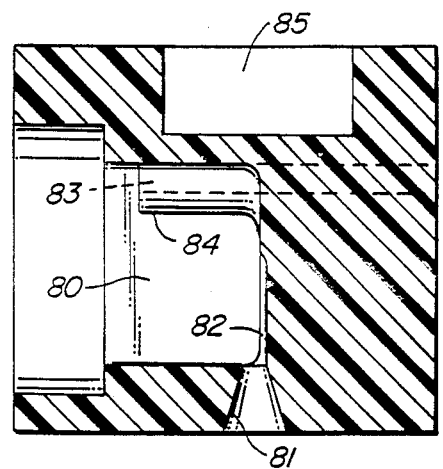
FIG._4A.   FIG._4B.

APPARATUS FOR CAPILLARY ELECTROPHORESIS

BACKGROUND OF THE INVENTION

This invention relates to capillary electrophoresis, and in particular to structures for holding capillary tubes. Aligning the tubes in the light path for directing liquid flows, and securing electrical contacts for electrophoretic separations in such tubes.

Capillary electrophoresis offers advantages over other types of electrophoresis for certain applications. These advantages include the separation of extremely small samples, a long separation path permitting the separation of a multitude of components in a single sample including those which are closely related, and the use of a high voltage to achieve the separation in a relatively short period of time. Capillary tubes further permit on-line detection of the separated species by passing a light beam through the tube at a point towards its exit end, and directing the emerging light beam to a detector.

Difficulties associated with the use of capillary tubes include the awkwardness of handling involved in sample injection, in connecting and disconnecting the tubes to anolyte and catholyte solutions, and in changing the anolyte and/or catholyte solutions for purposes of zone mobilization and other procedures involved in the separations. A further difficulty is in controlling the Joule heating caused by the high voltage and the zone broadening which often occurs as a result. In the case of on-line detection, difficulties arise in achieving and maintaining proper alignment of the tube in the optical path of a detector and avoidance of drift due to the Joule heating.

SUMMARY OF THE INVENTION

The present invention resides in various aspects of a readily assembled apparatus which addresses the difficulties delineated above. A capillary tube cartridge is provided which promotes stabilization and evening out of the temperature throughout the capillary tube and maintains alignment of the tube with an optical path while protecting the tube against external exposure and breakage. The cartridge is provided with mating members at the capillary termini suitable for joining the capillary with inlet and outlet blocks, each block containing a buffer chamber fitted with an electrode and containing an overflow port to maintain equal hydrostatic head at both ends of the column. The inlet block is further equipped with an injection port for buffer loading, capillary loading and sample injection. Thus, all preparatory loadings, as well as the electrophoresis itself and any post-separation steps needed for zone mobilization may be performed without removing the inlet or outlet blocks from the cartridge.

BRIEF DESCRIPTION OF THE DRAWINGS

FIG. 1 is an exploded perspective view of examples of several aspects of the invention, demonstrating how they may be combined for use in electrophoresis.

FIG. 2 is a perspective view of an example of a capillary tube cartridge in accordance with the present invention, shown in halves opened to reveal the interior of the cartridge.

FIG. 3, parts a through d, are a plan view and three sectional views of the inlet block shown in FIG. 1.

FIG. 4, parts a and b, are a plan view and a sectional view of the outlet block shown in FIG. 1.

DETAILED DESCRIPTION OF THE INVENTION AND PREFERRED EMBODIMENTS

FIG. 1 depicts a capillary tube cartridge 10 and associated components and fittings utilized to perform electrophoresis and zone detection in the capillary. These components and fittings include an inlet block 11, an outlet block 12, a support block 13 to hold the cartridge and inlet and outlet blocks in position, an inlet end electrode 14, an outlet end electrode 15, a light source 16, and a photocell 17. Also shown are entry side and exit side lenses 18, 19, retained by the cartridge to direct light from the light source 16 through a light passage in the capillary where it is interceded by the capillary, and then toward the photocell 17. An injection fitting 20 for injection of liquids into the inlet block 11 is shown, as well as a valve stem 21 for controlling fluid flows through the inlet block 11. A securing screw 22 presses the inlet block 11 against the cartridge 10 on one side, and a spring 23 presses the outlet block 12 against the cartridge 10 on the other side, to communicate these blocks with the capillary tube in the cartridge in a fluid-tight manner while ensuring alignment of the light passage through the cartridge with the light source 16 and the detector 17.

Assembly of the parts for this particular embodiment is achieved by inserting the inlet and outlet blocks in respective block recesses 24, 25 in the support block, with the spring 23 in place on the outward-facing side of the outlet block and the securing screw 22 in a full open position, which draws the inlet block outward. The cartridge 10 is then inserted, its orientation insured by a guide 26, which protrudes from both sides of the cartridge although only one side is visible in the drawing. The cartridge is inserted in the orientation shown but with its right side edge (according to the view shown) extending into the inlet block recess 24 to accommodate the guide 26. When the cartridge is fully lowered, the guide 26 is aligned with a horizontal groove (not shown in the drawing) in the interior of the support block 13, which permits lateral sliding of the cartridge. The securing screw 22 is then tightened, pushing the inlet block 11 toward the center of the support block, the inlet block in turn forcing the cartridge 10 to the left. A boss 27 protruding from the cartridge then abuts a stop (not shown) in the support block interior which insures proper alignment of the cartridge with the light source 16 and detector 17.

FIG. 2 shows the capillary tube cartridge 10 in separated form. The cartridge is generally formed of two flat plates 30, 31, generally rectangular in shape, with raised edges 32, 33 along the entire border of each. When the cartridge is assembled, the two plates are joined with the sides visible in the Figure facing one another and the raised edges 32, 33 in contact. The recessed portions 34, 35 defined by the raised edges 32, 33 thus combine to form an internal chamber having a depth (in the direction normal to the planes of the two plates 30, 31) of considerably lesser magnitude than its length or width. The depth will be sufficient to accommodate the capillary tube 36 looped over itself as shown, with a minimum of excess depth. In most applications, an appropriate depth will be approximately 0.05 inch (0.13 cm) or less. The depth is supported at the center of the chamber by internal bosses 37, 38 at opposing locations in the recesses of the two plates, respectively, each substantially equal in height to that of each of the raised edges 32, 33, for added protection of the capillary. Adhesive material is placed at selected locations 39, 40, 41, 42 to secure the two plates 30, 31 together.

The capillary tube 36 is retained inside the chamber formed by the two plates in a looped configuration, with at least one loop. In the embodiment shown in FIG. 2, the tube forms a double loop. The loop(s) are arranged to extend over most of the area of the broad dimensions (length and width) of the cartridge, each portion of the loop having maximum proximity to at least one of the two plates 30, 31 forming the cartridge. The termini of the capillary (not visible in the Figure) are embedded in cone-shaped members 43, 44, shaped and sized to mate with cone-shaped ports in the inlet and outlet blocks, respectively (described further below), thereby providing fluid-tight connections for communication of the capillary passage with the exterior of the cartridge. The looped capillary is held in place by adhesive 45 placed at various points along the loop to secure it to one of the plates.

Each of the two cartridge plates 30, 31 has a window 46, 47, respectively, positioned such that when the plates are joined, the windows are in alignment, forming a light path perpendicular to the planes of the plates, traversing the capillary tube at a detection point close to one end of the capillary. The capillary will be arranged in the cartridge such that the detection point is on the downstream side of the loop in the direction of the electrophoretic flow, or of the zone mobilization in cases where the zones are first focused by isoelectric focusing, then mobilized for detection purposes. Each window is sized and shaped to retain a lens 18, 19, as shown in FIG. 1. The selection of the lenses is not critical to the present invention, and may vary with the particular application. In most cases, however, the lens in the plate at the entry side of the cartridge will be a concave lens focusing the light toward the lens in the plate at the exit side, and the latter will be a ball lens.

The cartridge plates 30, 31 are constructed with a broad surface area and substantially planar shape, which promote the stabilization and evening out of temperature differences along the capillary tube length. The use of plate material having expansion rates similar to epoxy and glass, together with the configuration of the plates, i.e., their length and width being of relatively large dimensions compared to the depth of the chamber formed between them, contribute to these thermal regulating effects without the need for a coolant medium. As a result, the remaining space in the chamber will generally be occupied by air. As an alternative, however, the cartridge may be filled with a liquid heat transfer medium, to further equalize the temperature throughout the tube. Fluid ports (not shown in the drawings) may be included in the cartridge plates as inlets and outlets for the liquid.

The avoidance of drift of the components in the light path and the maintenance of fluid-tight seals as well as the achievement of reproducibility in the electrophoretic separations and readings is further enhanced by the proper selection of materials for the parts in contact with the capillary tube. These parts include the two plates 30, 31, the mating cones 43, 44, and the lenses 18, 19. The capillary tube itself will be of transparent material, generally glass or plastic, preferably fused silica. Preferred materials for the contacting parts will be those which are thermally compatible, with approximately equal coefficients of thermal expansion. Preferred compatible materials are glass-filled plastics, particularly glass-filled liquid crystal, for the cartridge plates 30, 31 and the mating cones 43, 44, and glass for the lenses 18, 19.

The capillary is further secured in position transversing the light path by a laminated arrangement of metal plates 48, surrounding the segment of the capillary containing the detection point, and bonded to each of the cartridge plates 30, 31. The metal plates have windows aligned with the light path. In the arrangement shown, the metal lamination is comprised of three layers, the inner layer being split to permit passage of the capillary. The metal further serves to dissipate heat at the detection point, where excess heat is generated by the detection light beam.

The inlet block 11 is shown in detail in FIG. 3, parts a through d. FIG. 3a is a plan view, and FIGS. 3b, 3c and 3d are sectional views taken along lines A—A, B—B and C—C, respectively, of FIG. 3a. This block is a solid block of a single piece of material, which may be formed in any conventional manner, such as machining or molding. The block is formed to define three recesses. The first such recess is a reservoir 60 for a buffer solution serving as the electrolyte used to apply the current for the electrophoresis. The second is an injection port 61 for the introduction of fluids into the buffer reservoir 60 and the capillary tube. The third is an outlet port 62, which is cone-shaped to mate with the cone-shaped mating member 43 on the capillary tube cartridge at the inlet terminus of the capillary tube.

The three reservoirs are connected by ducts 63, 64, 65 which meet at a common junction 66. The first duct communicates the buffer reservoir 60 to the junction. This duct is open to the exterior of the block and contains a conical portion 67 serving as a valve seat to mate with a conical tip of the valve stem 21 shown in FIG. 1. When the valve stem is fully tightened against the seat, the first duct 63 is closed off, interrupting fluid communication between the buffer reservoir 60 and the remaining recesses in the block. The remaining ducts 64, 65 communicate the injection port 61 and the outlet port 62, respectively, with the first duct 63 through the common junction 66.

The buffer reservoir 60 communicates with an overflow passage 69 separated from the reservoir by a separating wall 70 of a height preselected to establish a hydrostatic head of a selected magnitude in the capillary column, and to permit flushing out of the ducts and the buffer reservoir when desired. The mouth of the buffer reservoir is shaped to receive and support the electrode 14 shown in FIG. 1.

A recess 68 exists for the securing screw 22, shown in FIG. 1. The recess is elongated and open at one end to permit the block to be slid over a securing screw with an expanded end.

The outlet block 12 is shown in detail in FIG. 4, of which part a is a plan view and part b is a sectional view along the line D—D of part a. This block contains a buffer reservoir 80 in fluid communication with an outlet port 81, which, like the outlet port 62 of the inlet block 11, is cone-shaped to mate with the cone-shaped mating member 44 on the capillary tube cartridge at the outlet terminus of the capillary tube. A trough 82 facilitates the flow between the buffer reservoir and the outlet port. An overflow passage 83 and separating wall 84, similar to those in the inlet block, establish the hydrostatic head in the capillary, which is arranged to be equal to that in the inlet block. A recess 85 is arranged to receive and guide the securing spring 23 shown in FIG. 1.

To prepare the system for electrophoresis, the parts are assembled as shown in FIG. 1, and the buffer reservoirs in both the inlet and outlet blocks are filled with buffer solution. The valve stem 21 is then closed, sealing off the buffer reservoir in the inlet block from the remaining portions of the inlet block. The capillary tube is then filled with buffer solution from the injection port by the use of a manual syringe, using the injection fitting shown in FIG. 1. A pressure on the order of 1000 psi will generally be required to force the solution through the tube. Once the tube is filled, the syringe is removed and the valve adjoining the reservoir is opened. A syringe with sample is then placed in the injection port, and sample is introduced into the junction region 66 in the inlet block. With the valve still open, voltage is then applied across the capillary to introduce the sample into the capillary electrophoretically. Once the sample is inside the capillary, the ducts are flushed out to remove residual sample or other materials, which pass out of the block through the overflow passage 69.

The foregoing is offered primarily for purposes of illustration. It will be readily apparent to those skilled in the art that variations, modifications, and substitutions in the components described and depicted herein may be made without departing from the spirit and scope of the invention.

What is claimed is:

1. A capillary tube cartridge for high performance electrophoresis, comprising:
    a housing comprised of two substantially flat plates bonded together along their borders to define an enclosed chamber having a depth of about 0.05 inch or less normal to said plates, each said plate having a window arranged therein such that said windows are aligned to provide a light path through said housing normal to said plates; and
    a capillary tube disposed inside said enclosed chamber and arranged therein to pass through said light path, said capillary tube having first and second ends adjoined respectively to first and second ports in said housing, thereby communicating said capillary tube with the exterior of said housing.

2. A capillary tube cartridge in accordance with claim 1, in which said capillary tube is coiled inside said housing to form at least one loop.

3. A capillary tube cartridge in accordance with claim 1, in which said first and second ports have axes substantially parallel to said plates, and are positioned along the borders of said plates.

4. A capillary tube cartridge in accordance with claim 1, in which said first and second ports have axes substantially parallel to said plates, and are positioned at opposing positions along the borders of said plates.

5. A capillary tube cartridge in accordance with claim 1, further comprising a heat dissipating metallic enclosure disposed inside said chamber surrounding the portion of said capillary tube passing through said light path.

6. A capillary tube cartridge in accordance with claim 1, in which said plates are defined as housing plates and said capillary tube cartridge further comprises a pair of heat dissipating metallic plates each having an orifice, said metallic plates arranged inside said chamber in contact with and on either side of said capillary tube adjacent to said windows such that said orifices are aligned with said light path.

7. A capillary tube cartridge for high performance electrophoresis, comprising:
    a housing comprised of two substantially flat plates defined as housing plates, said housing plates bonded together along their borders to define an enclosed chamber having a depth of about 0.05 inch or less normal to said housing plates, each said housing plate having a window arranged therein such that said windows are aligned to provide a light path through said housing normal to said housing plates, each said window containing a lens;
    a capillary tube disposed inside said enclosed chamber and arranged therein to form at least one loop, said capillary tube having first and second ends adjoined respectively to first and second ports in said housing, thereby communicating said capillary tube with the exterior of said housing, said first and second ports having axes substantially parallel to said housing plates and positioned at opposing positions along the borders of said housing plates, said capillary tube further being arranged such that a portion thereof outside of said loop passes through said light path; and
    a pair of heat dissipating metallic plates each having an orifice, said metallic plates arranged inside said chamber in contact with and on either side of said capillary tube adjacent to said windows such that said orifices are aligned with said light path.

8. A combination buffer reservoir and sample injection block for high performance capillary electrophoresis, comprising (a) a single block shaped to define therein:
    (i) a reservoir for buffer solution, adapted to receive an electrode;
    (ii) an injection port adapted for fluid-tight insertion therein of a syringe;
    (iii) an outlet port adapted for fluid-tight communication with a capillary column; and
    (iv) first, second and third ducts communicating said reservoir, injection port and outlet port, respectively, to a common junction inside said block;
    (b) valve means adapted to close said first duct to seal said reservoir off from said common junction, and
    (c) overflow means for permitting the escape of excess liquid flowing into said reservoir.

9. A combination buffer reservoir and sample injection block for high performance capillary electrophoresis, comprising (a) a single block shaped to define therein:
    (i) a reservoir for buffer solution, adapted to receive an electrode;
    (ii) an injection port adapted for fluid-tight insertion therein of a syringe;
    (iii) an outlet port adapted for fluid-tight communication with a capillary column; and
    (iv) first, second and third ducts orthogonal with respect to each other and communicating said reservoir, injection port and outlet port, respectively, to a common junction inside said block;
    (b) valve means adapted to close said first duct to seal said reservoir off from said common junction.

* * * * *